(12) United States Patent
Goodall et al.

(10) Patent No.: US 7,098,278 B2
(45) Date of Patent: *Aug. 29, 2006

(54) OLEFIN POLYMERIZATION CATALYST AND POLYMERIZATION PROCESS

(75) Inventors: Brian L. Goodall, Ambler, PA (US); Robert Howard Grubbs, South Pasadena, CA (US); Andrew Willis Waltman, Pasadena, CA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/345,745

(22) Filed: Feb. 2, 2006

(65) Prior Publication Data

US 2006/0128911 A1 Jun. 15, 2006

Related U.S. Application Data

(63) Continuation of application No. 11/054,631, filed on Feb. 9, 2005.

(60) Provisional application No. 60/556,802, filed on Mar. 26, 2004.

(51) Int. Cl.
*C08F 4/80* (2006.01)
*C07F 7/28* (2006.01)

(52) U.S. Cl. ............ 526/171; 526/160; 526/161; 526/170; 526/281; 526/352; 548/103; 502/103; 502/117; 502/155; 556/52

(58) Field of Classification Search ........... 548/103; 502/103, 117, 155; 526/160, 161, 171, 170, 526/281, 352
See application file for complete search history.

(56) References Cited

U.S. PATENT DOCUMENTS 5,637,660 A 6/1997 Nagy et al.
6,593,266 B1 7/2003 Matsui et al.
6,613,851 B1 9/2003 Jens et al.
6,888,002 B1 5/2005 Herrmann et al.
2002/0040115 A1 4/2002 Sen et al.
2002/0077477 A1 6/2002 Reichie et al.
2005/0215738 A1* 9/2005 Goodall et al. ............ 526/171

FOREIGN PATENT DOCUMENTS

WO WO 00/01739 A1 1/2000
WO WO 02/49758 A1 6/2002
WO WO 2004/002931 1/2004

OTHER PUBLICATIONS

Sellmann, Dieter et al; "Transition-Metal Complexes With Sulfur Ligands, 94. Synthesis and Reactivity of Nickel Palladium, and Platinum Complexes with the Thiolate Carbene Ligand '$S_2C$'$^{-2}$—. X-ray Stucture Determinations of [Ni(PMe$_3$) ('$S_2C$'), [Ni(PPh$_3$) ('$S_2C$')], [Ni('SC')$_2$], Pt(PMe$_3$)('$S_2C$'), and ('$S_2CO$')$_2^+$", Inorganic Chemistry, 32(5), 538-46 CODEN: INOCAJ; ISSN; 0020-1669, 1993, XP008049070.

Ketz, Benjamin E. et al; "Structure and Reactivity of an Allylpalladium N-Heterocyclic Carbene Enolate Complex Structure and Reactivity of an Allylpalladium N-Heterocyclic Carbene Enolate Complex", Organometallics, 23(12), 2835-2837 CODEN; ORGND7; ISSN; 0276-7333, 2004, XP008049060.

Waltman, Andrew et al; "A New Class of Chelating N-Heterocyclic Carbene Ligands and Their Complexes with Palladium" Organometallics, 23(13), 3105-3107 CODEN; ORGAN7; ISSN: 0276-733, 2004, XP00804901.

* cited by examiner

*Primary Examiner*—Fred Teskin
(74) *Attorney, Agent, or Firm*—Thomas S. Deibert

(57) ABSTRACT

A polymerization catalyst for the polymerization and copolymerization of olefin monomers and the copolymerization of olefin monomers with other monomers selected from, for example, norbornenes and styrenes are disclosed. The polymerization catalysts disclosed contain a metal center selected from Ti, Zr, Hf, Ni and Pd with at least one chelating ligand.

9 Claims, No Drawings

OLEFIN POLYMERIZATION CATALYST AND POLYMERIZATION PROCESS

This application is a continuation of prior U.S. patent application Ser. No. 11/054,631, filed Feb. 9, 2005 now U.S. Pat. No. 7,037,987, which application claims the benefit of U.S. Provisional Application Ser. No. 60/556,802, Mar. 26, 2004.

The present invention relates to a polymerization catalyst useful for the polymerization and copolymerization of olefins. The present invention also relates to olefin polymerization and copolymerization processes using such polymerization catalysts.

Polymers and copolymers of olefins generally exhibit excellent mechanical properties suitable for use in many fields of application. These materials have become so widely used it is hard to imagine life without them. Light, waterproof and resistant to corrosion, they are frequently the designer's first choice for such disparate items such as water pipes, trash bags, hair combs, fibers for clothing and road construction, automobile body parts, and packaging for food and medicine.

One class of catalysts for the polymerization and copolymerization of olefins is disclosed by Matsui et al. in U.S. Pat. No. 6,593,266. Matsui et al. disclose a catalyst that contains (A) a transition metal compound represented by the general formula (i) and, optionally, (B) at least one compound selected from an organometallic compound, an organoaluminum oxycompound and a compound that reacts with the transition metal compound (A) to form an ion pair. Formula (i) is disclosed by Matsui et al. as follows:

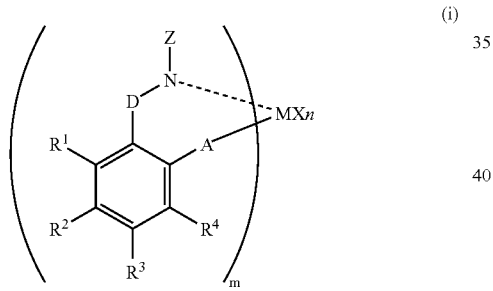

(i)

wherein M is a transition metal atom selected from Group 3 to Group 11 of the periodic table; m is an integer from 1 to 6; A is —O—, —S—, —Se—, or —N($R^5$)—; D is —C($R^7$)($R^8$)—, —Si($R^9$)($R^{10}$)—, or the like; Z is —$R^{13}$ and —$R^{14}$, =C($R^{15}$)$R^{16}$, =N$R^{17}$ or the like, $R^1$ to $R^{17}$ are each selected from H, a hydrocarbon group or the like; n is a number satisfying a valence of M; and X is a halogen, a hydrocarbon group or the like.

Notwithstanding, a need still exists for new olefin polymerization catalysts that exhibit high polymerization activity. There also exists a need for catalysts for the polymerization of ethylene that provides a substantially linear product (i.e. polyethylene with a lower degree of branching). There further exists a need for catalysts that will enable the preparation of substantially linear polymers while exhibiting tolerance to polar impurities such that they are capable of copolymerizing monomers bearing polar substituents. The polymerization catalysts of the present invention may satisfy one or more of these needs.

In one aspect of the present invention there is provided a polymerization catalyst comprising: a metal center selected from titanium (Ti), zirconium (Zr), hafnium (Hf), nickel (Ni) and palladium (Pd) with at least one chelating ligand comprising a carbene with at least one anionic moiety, wherein the at least one chelating ligand has a structure selected from formula I to IV

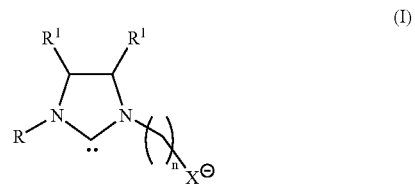

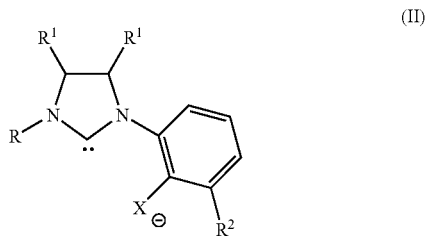

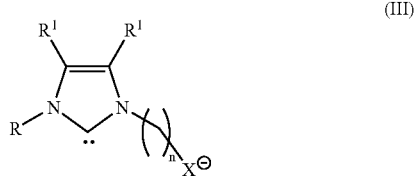

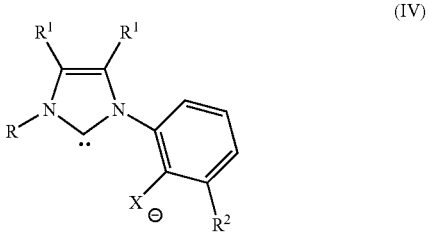

wherein R is any hydrocarbyl group; each $R^1$ is independently any hydrocarbyl group; $R^2$ is any hydrocarbyl group; and X is selected from oxygen, nitrogen and sulfur; wherein both the carbene and the anionic moiety are coordinated to the metal center.

In another aspect of the present invention, there is provided a process for preparing a homopolymer comprising contacting at least one α-olefin monomer with a polymerization catalyst in the presence of an aluminum activator, wherein the polymerization catalyst comprises: a metal center selected from titanium (Ti), zirconium (Zr) and hafnium (Hf) with two chelating ligands comprising a carbene with at least one anionic moiety, wherein each of the chelating ligands have a structure independently selected from formula I to IV; wherein R is any hydrocarbyl group; each $R^1$ is independently any hydrocarbyl group; $R^2$ is any hydrocarbyl group; and X is selected from oxygen, nitrogen and sulfur; wherein both the carbene and the anionic moiety are coordinated to the metal center.

In another aspect of the present invention, there is provided a process for preparing a copolymer comprising contacting at least two different monomers selected from α-olefins, norbornenes and styrenes with a polymerization catalyst in the presence of an aluminum activator, wherein the polymerization catalyst comprises: a metal center selected from titanium (Ti), zirconium (Zr) and hafnium (Hf) with two chelating ligands comprising a carbene with at least one anionic moiety, wherein each of the chelating ligands have a structure independently selected from formula I to IV; wherein R is any hydrocarbyl group; each $R^1$ is independently any hydrocarbyl group; $R^2$ is any hydrocarbyl group; and X is selected from oxygen, nitrogen and sulfur; wherein both the carbene and the anionic moiety are coordinated to the metal center.

In another aspect of the present invention, there is provided a process for preparing a homopolymer comprising contacting ethylene with a polymerization catalyst, optionally in the presence of an aluminum activator, wherein the polymerization catalyst comprises a metal center selected from nickel (Ni) and palladium (Pd) with a chelating ligand comprising a carbene with at least one anionic moiety, wherein the chelating ligand has a structure selected from formula I to IV; wherein R is any hydrocarbyl group; each $R^1$ is independently any hydrocarbyl group; $R^2$ is any hydrocarbyl group; and X is selected from oxygen, nitrogen and sulfur; wherein both the carbene and the anionic moiety are coordinated to the metal center.

In another aspect of the present invention, there is provided a process for preparing a copolymer comprising contacting ethylene, an acrylic monomer and a polymerization catalyst, optionally in the presence of an aluminum activator, wherein the polymerization catalyst comprises a metal center selected from nickel (Ni) and palladium (Pd) with a chelating ligand comprising a carbene with at least one anionic moiety, wherein the chelating ligand has a structure selected from formula I to IV; wherein R is any hydrocarbyl group; each $R^1$ is independently any hydrocarbyl group; $R^2$ is any hydrocarbyl group; and X is selected from oxygen, nitrogen and sulfur; wherein both the carbene and the anionic moiety are coordinated to the metal center.

In another aspect of the present invention, there is provided a process for preparing a copolymer comprising contacting a polymerization catalyst with at least two different monomers selected from α-olefins, norbornenes and styrenes in the presence of an aluminum activator, wherein the polymerization catalyst comprises: a metal center selected from titanium (Ti), zirconium (Zr) and hafnium (Hf) with two chelating ligands comprising a carbene with at least one anionic moiety, wherein each of the chelating ligands have a structure independently selected from formula I to IV; wherein R is any hydrocarbyl group; each $R^1$ is independently any hydrocarbyl group; $R^2$ is any hydrocarbyl group; and X is selected from oxygen, nitrogen and sulfur; wherein both the carbene and the anionic moiety are coordinated to the metal center.

In one embodiment of the present invention, the polymerization catalyst includes a metal center selected from titanium (Ti), zirconium (Zr) and hafnium (Hf) with two halide ligands and two chelating ligands; wherein the two halide ligands are independently selected from chlorine (Cl), bromine (Br) and iodine (I); wherein each chelating ligand comprises a carbene with at least one anionic moiety and wherein each chelating ligand has a structure independently selected from formula I to IV

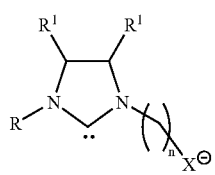
(I)

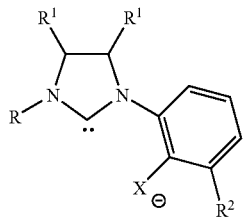
(II)

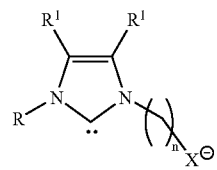
(III)

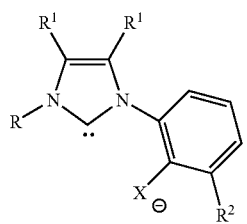
(IV)

wherein R may be any hydrocarbyl group, alternatively R may be selected from a hydrocarbon and an aromatic; each $R^1$ may independently be any hydrocarbyl group, alternatively each $R^1$ may independently be selected from hydrogen (H) and methyl (Me), alternatively each $R^1$ forms part of a cyclic aromatic or hydrocarbon group; $R^2$ may be any hydrocarbyl group, alternatively $R^2$ may be selected from hydrogen (H), methyl (Me), t-butyl, adamantyl, phenyl (Ph) and anthracenyl; and X is selected from oxygen, nitrogen and sulfur; wherein both the carbene and the anionic moiety are coordinated to the metal center. In one aspect of this embodiment, the polymerization catalyst may have a structure selected from formula (V) and (VI)

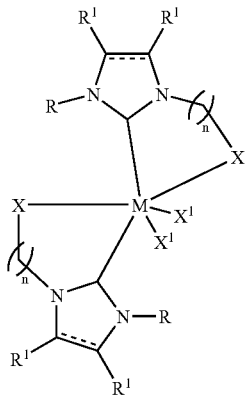
(V)

-continued (VI)

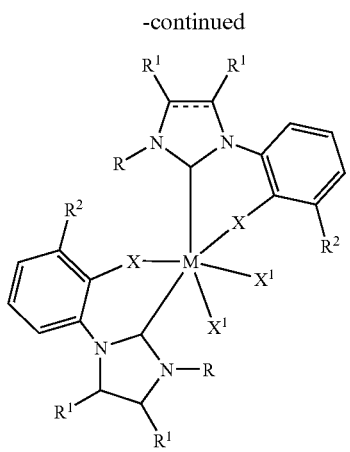

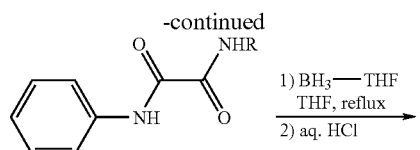

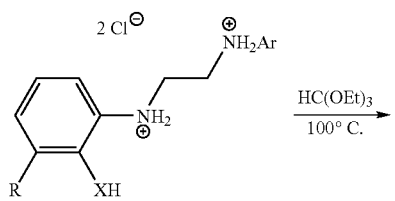

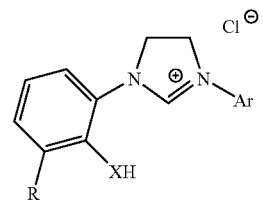

Alternatively:

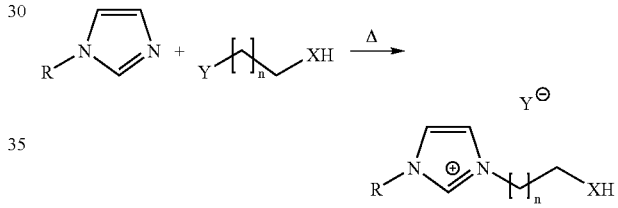

wherein R, $R^1$, $R^2$, M and X are as defined above for this embodiment and wherein each $X^1$ is a halide ligand independently selected from wherein the two halide ligands are independently selected from chlorine (Cl), bromine (Br) and iodine (I).

In another embodiment of the present invention, the polymerization catalyst includes a metal center selected from nickel (Ni) and palladium (Pd) with a chelating ligand; wherein the chelating ligand comprises a carbene with at least one anionic moiety and wherein each chelating ligand has a structure independently selected from formula I to IV; wherein R may be any hydrocarbyl group, alternatively R may be selected from a hydrocarbon and an aromatic; each $R^1$ may independently be any hydrocarbyl group, alternatively each $R^1$ may independently be selected from hydrogen (H) and methyl (Me), alternatively each $R^1$ forms part of a cyclic aromatic or hydrocarbon group; $R^2$ may be any hydrocarbyl group, alternatively $R^2$ may be selected from hydrogen (H), methyl (Me), t-butyl, adamantyl, phenyl and anthracenyl; and X is selected from oxygen, nitrogen and sulfur; wherein both the carbene and the anionic moiety are coordinated to the metal center. In one aspect of this embodiment, the polymerization catalyst further comprises a hydrocarbyl ligand and a neutral ligand coordinated with the metal center; wherein the hydrocarbyl ligand is selected from methyl (Me), phenyl (Ph) and mesityl and wherein the neutral ligand is selected from phosphine, amine and pyridine. In another aspect of this embodiment, the polymerization catalyst further comprises a chelating hydrocarbyl ligand coordinated with the metal center.

The chelating ligands of the present invention comprising a carbene with at least one anionic moiety may be prepared, for example, using the synthesis method depicted in the following equations:

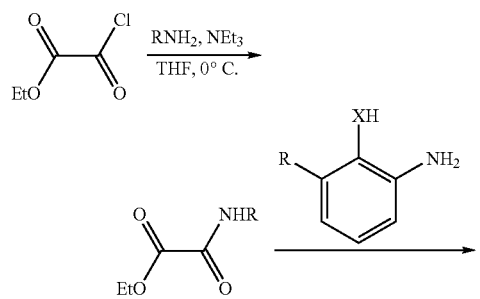

Chelating hydrocarbyl ligands suitable for use with the present invention include allyl, linear and branched $C_3$–$C_{20}$ alkenyl, $C_6$–$C_{15}$ cycloalkenyl, allylic ligands or canonical forms thereof, optionally substituted with hydrocarbyl and/or heteroatom substituents selected from linear or branched $C_1$–$C_5$ alkyl, linear or branched $C_1$–$C_5$ haloalkyl, linear or branched $C_2$–$C_5$ alkenyl and haloalkenyl, halogen, sulfur, oxygen, nitrogen, phosphorus, and phenyl optionally substituted with linear or branched $C_1$–$C_5$ alkyl, linear or branched $C_1$–$C_5$ haloalkyl, and halogen; wherein the cycloalkyl and cycloalkenyl groups may be monocyclic or multicyclic; wherein the aryl groups can be a single ring (e.g., phenyl) or a fused ring system (e.g., naphthyl); wherein the cycloalkyl, cycloalkenyl and aryl groups can be taken together to form a fused ring system; and wherein each of the monocyclic, multicyclic and aryl ring systems may optionally be monosubstituted or multisubstituted with a substituent independently selected from hydrogen, linear and branched $C_1$–$C_5$ alkyl, linear and branched $C_1$–$C_5$ haloalkyl, linear and branched $C_1$–$C_5$ alkoxy, chlorine, fluorine, iodine, bromine, $C_5$–$C_{10}$ cycloalkyl, $C_6$–$C_{15}$ cycloalkenyl and $C_6$–$C_{30}$ aryl.

In one aspect, the chelating hydrocarbyl ligand may be selected from the group of structures depicted in Structures A–E bound to a metal center M or a metal center with a ligand M(L).

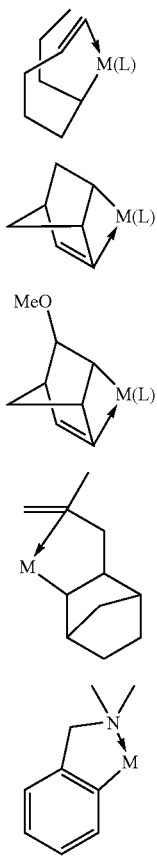

Structure A

Structure B

Structure C

Structure D

Structure E

Monomers suitable for use with the present invention include α-olefins, norbornenes, styrenes and (meth)acrylates.

α-Olefins suitable for use with the present invention include, for example, ethylene, propylene, 1-butene, 1-hexene and 1-octene. Norbornene-type monomers suitable for use with the present invention include, for example, norbornenes bearing polar groups such as carboxylic acid ester. The term "norbornene-type monomer" as used herein and in the appended claims is meant to encompass norbornene, substituted norbornene, as well as any substituted and unsubstituted higher cyclic derivatives thereof, provided that the subject monomer contains at least one norbornene-type moiety or substituted norbornene-type moiety.

Norbornene-type monomers suitable for use with the present invention may include substituted norbornene-type monomers and higher cyclic derivatives thereof that contain a pendant hydrocarbyl substituent or a pendant functional substituent containing an oxygen atom.

Norbornene-type monomers suitable for use with the present invention may include norbornene-type or polycyclooelfin monomers are represented by the structure below:

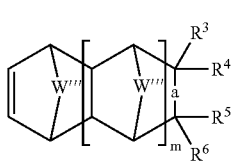

(VII)

wherein W''' is selected from the group including, but by no means limited to, an oxygen, a nitrogen with a hydrogen attached thereto, a nitrogen with a linear $C_1$ to $C_{10}$ alkyl grouping attached thereto, a nitrogen with a branched $C_1$ to $C_{10}$ alkyl grouping attached thereto, a sulfur and a methylene group of having the formula —$(CH_2)n'$— wherein n' is an integer from 1 to 5, "a" is a single or a double bond; $R^3$, $R^4$, $R^5$, and $R^6$ each independently represent a hydrogen, a hydrocarbyl or a functional substituent; m is an integer from 0 to 5, with the proviso that when "a" is a double bond, both (i) one of $R^3$ and $R^4$ is not present and (ii) one of $R^5$ and $R^6$ is not present.

The term "hydrocarbyl groups" as used herein and in the appended claims encompasses hydrogen, hydrocarbyl groups, halohydrocarbyl groups, perhalohydrocarbyl groups and perhalocarbyl groups. In one embodiment, $R^3$, $R^4$, $R^5$ and/or $R^6$, may independently represent hydrogen, linear or branched $C_1$–$C_{10}$ alkyl, linear or branched $C_2$–$C_{10}$ alkenyl, linear or branched $C_2$–$C_{10}$ alkynyl, $C_4$–$C_{12}$ cycloalkyl, $C_4$–$C_{12}$ cycloalkenyl, $C_6$–$C_{12}$ aryl, and $C_7$–$C_{24}$ aralkyl. In one embodiment, $R^3$ and $R^4$ or $R^5$ and $R^6$ may collectively represent a $C_1$–$C_{10}$ alkylidenyl group. Representative alkyl groups include, but are by no means limited to, methyl, ethyl, propyl, isopropyl, butyl, isobutyl, sec-butyl, tert-butyl, pentyl, neopentyl, hexyl, heptyl, octyl, nonyl and decyl. Representative alkenyl groups include, but are by no means limited to, vinyl, allyl, butenyl and cyclohexenyl. Representative alkynyl groups, include but are by no means limited to, ethynyl, 1-propynyl, 2-propynyl, 1-butynyl and 2-butynyl. Representative cycloalkyl groups include, but are by no means limited to, cyclopentyl, cyclohexyl and cyclooctyl substituents. Representative aryl groups include, but are by no means limited to, phenyl, naphthyl and anthracenyl. Representative aralkyl groups include, but are by no means limited to, benzyl and phenethyl. Representative alkylidenyl groups include, but are by no means limited to, methylidenyl and ethylidenyl groups.

When the pendant group(s) is(are) a functional substituent, $R^3$, $R^4$, $R^5$ may $R^6$ independently represent a radical selected from $(CH_2)_n$—$CH(CF_3)_2$—O—$Si(Me)_3$, —$(CH_2)_n$—$CH(CF_3)_2$—O—$CH_2$—O—$CH_3$, —$(CH_2)_n$—$CH(CF_3)_2$—O—C(O)—O—$C(CH_3)_3$, —$(CH_2)_n$—$C(CF_3)_2$—OH, —$(CH_2)_nC(O)NH_2$, —$(CH_2)_nC(O)Cl$, —$(CH_2)_nC(O)OR^7$, —$(CH_2)_n$—$OR^7$, —$(CH_2)_n$—$OC(O)R^7$, —$(CH_2)_n$—$C(O)R^7$, —$(CH_2)_n$—$OC(O)OR^7$, —$(CH_2)_n$Si$(R^7)_3$, —$(CH_2)_n$Si$(OR^7)_3$, —$(CH_2)_n$—O—Si$(R^7)_3$ and —$(CH^2)_nC(O)OR^8$ wherein n independently represents an integer from 0 to 10 and $R^7$ independently represents hydrogen, linear or branched $C_1$–$C_{20}$ alkyl, linear or branched $C_1$–$C_{20}$ halogenated or perhalogenated alkyl, linear or branched $C_2$–$C_{10}$ alkenyl, linear or branched $C_2$–$C_{10}$ alkynyl, $C_5$–$C_{12}$ cycloalkyl, $C_6$–$C_{14}$ aryl, $C_6$–$C_{14}$ halogenated or perhalogenated aryl, and $C_7$–$C_{24}$ aralkyl. Representative hydrocarbyl groups set forth under the definition of $R^7$ are the same as those identified above under the definition of $R^3$ to $R^5$. As set forth above under $R^3$ to $R^6$ the hydrocarbyl groups defined under $R^7$ may be halogenated and perhalogenated. Aluminum activators suitable for use with the present invention include, for example, methaluminoxane, isobutylaluminoxanes, hydroxyisobutylaluminoxane, hydrocarbylhaloaluminoxanes such as those described in WO 2003082466 and ionic aluminoxanates such as those described in WO 2003082879.

Some embodiments of the present invention will now be described in detail in the following Examples.

EXAMPLE 1

Synthesis of N-(mesityl)-oxanilic acid ethyl ester 2,4,6-Trimethylaniline (20 ml, 142 mmol, 1.0 equiv) and triethylamine (20 ml, 143 mmol, 1 equiv) were dissolved in dry tetrahydrofuran ("THF") (150 ml), forming a solution. The solution was cooled to 0° C., and ethyl chlorooxoacetetate (15.3 ml, 142 mmol, 1.0 equiv) was added slowly via syringe. Precipitation of a white solid occurred immediately upon addition of the ethyl chlorooxoacetate. The solution was allowed to stir overnight, warming to room temperature. The solid was then filtered off, and the organic layer was washed with 2 M HCl solution (2×100 ml). The aqueous layer was washed with ethyl acetate, and the combined organic layers were washed with brine (100 ml), and dried over $MgSO_4$. The solvent was then removed under reduced pressure, leaving a yellowish solid. The yellowish solid was recrystallized from hexanes/EtOAc (9:1), producing a product, white crystalline solid (30.15 g, 128 mmol, 90% yield). $^1$H NMR (300 MHz, $CDCl_3$) δ 8.34 (s, 1H), 6.92 (s, 2H), 4.43 (q, J=7.2 Hz, 2H), 2.28 (s, 3H), 2.20 (s, 6H), 1.45 (t, J=7.2 Hz, 3H); $^{13}$C NMR (75 MHz, $CDCl_3$) δ161.2, 154.9, 138.0, 134.9, 129.7, 129.3, 63.8, 21.2, 18.6, 14.3. Anal. Calcd for $C_{13}H_{17}NO_3$: C, 66.36; H, 7.28; N, 5.95. Found: C, 66.56; H, 7.15; N, 6.04.

EXAMPLE 2

Synthesis of N-(2,6-diisopropylphenyl)-oxanilic acid ethyl ester 2,6-Diisopropylaniline (90%) (10 ml, 48 mmol, 1.1 equiv) and triethylamine (7.3 ml, 48 mmol, 1 equiv) were dissolved in dry THF (150 ml), forming a solution. The solution was then cooled to 0° C., and ethyl chlorooxoacetetate (5.12 ml, 48 mmol, 1.0 equiv) was added slowly via syringe. Precipitation of a white solid occurred immediately upon addition of the ethyl chlorooxoacetate. The solution was allowed to stir overnight, warming to room temperature. The solid was then filtered off, and the organic layer was washed with 2 M HCl solution (2×100 ml). The aqueous layer was washed with ethyl acetate, and the combined organic layers were washed with brine (100 ml), and dried over $MgSO_4$. The solvent was then removed under reduced pressure, leaving a yellowish solid. The yellowish solid was then recrystallized from hexanes/EtOAc (9:1), producing a product, white crystalline solid (12.15 g, 44 mmol, 92% yield). $^1$H NMR (300 MHz, $CDCl_3$) δ 8.36 (s, 1H), 7.34 (t, J=7.1 Hz, 1H), 7.20 (d, J=7.8 Hz, 2H), 4.45 (q, J=7.2 Hz, 2H), 3.01 (septet, J=7.2 Hz, 2H), 1.47 (t, J=7.2 Hz, 3H), 1.21 (d, J=6.6 Hz, 12H); $^{13}$C NMR (75 MHz, $CDCl_3$) δ 161.3, 156.1, 146.1, 129.6, 129.2, 124.0, 63.9, 29.1, 23.9, 14.2. Anal. Calcd for $C_{16}H_{23}NO_3$: C, 69.29; H, 8.36; N, 5.05. Found: C, 69.31; H, 8.13; N, 5.10.

EXAMPLE 3

Synthesis of N-(mesityl)-N'-(2-hydroxyphenyl)-oxalamide

N-(Mesityl)-oxanilic acid ethyl ester (5.23 g, 24.4 mmol, 1 eq) and 2-aminophenol (2.67 g, 24.4 mmol, 1.0 eq) were dissolved in toluene (50 ml), forming a suspension. To this suspension was added triethylamine (6.8 ml, 50 mmol, 2 eq). The suspension was then heated to reflux, causing the solids to dissolve. After heating at reflux overnight, the product precipitated. At this point, ethyl acetate was added until the precipitate redissolved. The solution was then washed with 2 M HCl solution (2×100 ml). The aqueous layer was then washed with ethyl acetate, and the combined organic layers were washed with brine (100 ml), and dried over $MgSO_4$. The solvent was then removed under reduced pressure, leaving a yellowish solid. The yellowish solid was then recrystallized from toluene, producing a product, white crystalline solid (5.26 g, 17.7 mmol, 72.4% yield). $^1$H NMR (300 MHz, $CDCl_3$) δ 9.69 (s, 1H), 8.84 (s, 1H), 8.11 (s, J=7.7 Hz, 1H), 7.51 (dd, J=8.0, 1.8 Hz, 1H), 7.14 (ddd, J=1.5, 8.1, 7.2 Hz, 1H), 6.92 (m, 3H), 2.30 (s, 3H), 2.22 (s, 6H); $^{13}$C NMR (75 MHz, $CDCl_3$) δ 158.2, 157.9, 148.2, 138.2, 134.9, 129.5, 129.4, 127.7, 124.3, 122.2, 121.1, 118.9, 21.2, 18.6. Anal. Calcd for $C_{17}H_{18}N_2O_3$: C, 68.44; H, 6.08; N, 9.39. Found: C, 68.50; H, 5.96; N, 9.44.

EXAMPLE 4

Synthesis of N-(2,6-diisopropylphenyl)-N'-(2-hydroxyphenyl)-oxalamide

N-(2,6-Diisopropylphenyl)-oxanilic acid ethyl ester (2.78 g, 10 mmol, 1 eq) and 2-aminophenol (1.31 g, 12 mmol, 1.2 eq) were dissolved in toluene (50 ml), forming a suspension. To this suspension was added triethylamine (2.78 ml, 20 mmol, 2 eq). The suspension was then heated to reflux, causing the solids to dissolve. After heating at reflux overnight, the product precipitated. At this point, ethyl acetate was added until the precipitate redissolved. The solution was then washed with 2 M HCl solution (2×100 ml). The aqueous layer was then washed with ethyl acetate, and the combined organic layers were washed with brine (100 ml), and dried over $MgSO_4$. The solvent was then removed under reduced pressure, leaving a yellowish solid. The yellowish solid was then recrystallized from toluene, producing a product, white crystalline solid (2.9 g, 8.5 mmol, 85% yield). $^1$H NMR (300 MHz, $CDCl_3$) δ 9.67 (s, 1H), 8.84 (s, 1H), 8.12 (s, 1H), 7.50 (dd, J=8.25, 1.8 Hz 1H), 7.37 (t, J=7.2 Hz, 1H), 7.23 (d, J=7.5 Hz, 1H), 7.16 (dt, J=7.7, 1.5 Hz, 1H), 6.95 (comp m, 2H), 3.03 (septet, J=6.6 Hz, 2H), 1.22 (d, J=6.9, 12H); $^3$C NMR (75 MHz, $CDCl_3$) δ 158.9, 158.2, 148.2, 146.1, 129.4, 127.9, 124.2, 124.0, 122.3, 121.2, 119.1, 29.2, 23.9. Anal. Calcd for $C_{20}H_{24}N_2O_3$: C, 70.56; H, 7.11; N, 8.23; O, 14.10. Found: C, 34.90; H, 4.64; N, 5.79.

EXAMPLE 5

Synthesis of N-(mesityl)-oxanilic acid

N-(Mesityl)-oxanilic acid ethyl ester (1.99 g, 8.5 mmol) was dissolved in THF (50 ml), forming a solution. To this solution was added 1M NaOH solution (40 ml), and the mixture was then stirred for 2 hours. Diethyl ether (25 ml) was then added, and the layers were separated. The organic layer was washed with 1M NaOH solution (40 ml). The aqueous layer was then acidified with 2M HCl until precipitation occurred. The precipitate was then extracted with ethyl acetate (2×50 ml). The ethyl acetate was washed with brine (50 ml), and then dried over $MgSO_4$. Removal of the solvent under reduced pressure provided the product as a white solid (1.74 g, 8.4 mmol, 99% yield). $^1$H NMR (300 MHz, $CDCl_3$) δ 8.51 (s, 1H), 6.93 (s, 2H), 2.29 (s,3H), 2.19 (s, 6H); $^{13}$C NMR (75 MHz, $CDCl_3$) δ 160.0, 156.1, 138.6, 134.7, 129.5, 128.9, 21.2, 18.5. Anal. Calcd for $C_{11}H_{13}NO_3$: C, 63.76; H, 6.32; N, 6.76. Found: C, 63.59; H, 6.32; N, 6.79.

EXAMPLE 6

Synthesis of 2-Amino-4-methyl-6-tert-butylphenol 2-tert-Butyl-4-methylphenol (20.04 g, 122 mmol, 1.0 eq) is dissolved in AcOH (200 ml) and cooled to 0° C. A solution of concentrated nitric acid (7.73 ml, 122 mmol, 1 eq) in an equal volume of acetic acid was then added to the solution. Upon addition of the nitric acid, the solution turned yellow. After addition was complete, the solution was allowed to stir at 0° C. for 2.5 hours until some needles of product were observed to start growing. Deionized water (~25 ml) was then added, causing a great deal of precipitation. This was filtered, and water was again added to the filtrate, causing more precipitate that was again filtered. More precipitation/filtration cycles did not yield substantial further product. The orange/yellow solid obtained from the filtrations (13.06 g, 62.4 mmol, 51% yield) was dried overnight by vacuum. $^1$H NMR (300 MHz, CDCl$_3$) δ 11.40 (s, 1H), 7.77 (d, J=1.5 Hz, 1H), 7.37 (d, J=2.1 Hz, 1H), 2.31 (s, 3H), 1.42 (s, 9H); $^{13}$C NMR (75 MHz, CDCl$_3$) δ 153.3, 140.4, 136.3, 128.8, 122.5, 35.7, 29.6, 20.0. Anal. Calcd for C$_{11}$H$_{15}$NO$_3$: C, 63.14; H, 7.23; N, 6.69. Found: C, 64.52; H, 7.69; N, 5.89. A sample of this material, 2-amino-4-methyl-6-tert-butylphenol (4.13 g, 20 mmol, 1.0 eq), was then added to an oven dried, two-necked flask, and Pd (10% on charcoal) (1.051 g, 1 mmol Pd, 0.05 eq) was added. The flask was evacuated, and filled with argon, and then dry, degassed methanol (50 ml) was added. A balloon of hydrogen gas was placed over the reaction, and which was then allowed to stir for 16 hours. The solution was then filtered through celite, removing the Pd. The product was stable in inert atmosphere, but was observed to rapidly oxidize when in solution, exposed to air. The clear Pd/C suspension was observed to rapidly turn to a red solution upon filtration on the benchtop. The methanol was evaporated under reduced pressure, leaving a dark red solid. This dark red solid was then recrystallized from hexane to yield a whitish solid (2.41 g, 13.4 mmol, 68% yield) that was observed to slowly turn red while in the solid state. $^1$H NMR (300 MHz, CDCl$_3$) δ 6.67 (d, J=1.5 Hz, 1H), 6.61 (d, J=1.8 Hz, 1H), 5.57 (bs, 1H), 3.20 (bs, 2H), 2.22 (s, 3H), 1.40 (s, 9H); $^{13}$C NMR (75 MHz, CDCl$_3$) δ 144.1, 135.5, 133.4, 129.3, 120.7, 119.2, 34.6, 30.0, 21.2.

EXAMPLE 7

Synthesis of N-(mesityl)-N'-(2-hydroxy-3-tert-butyl-5-methylphenyl)-oxalamide N-(Mesityl)-oxanilic acid (2.15 g, 10.4 mmol, 1.0 eq), prepared according to the synthesis method described in Example 5, and 1-hydroxybenzotriazole (2.39 g, 15.6 mmol, 1.5 eq) were added to an oven dried, two-necked flask, forming a solution. THF (100 ml) was then added and the solution was cooled to 0° C. 1,3-dicyclohexylcarbodiimide (1 M in CH$_2$Cl$_2$) (12.5 ml, 12.5 mmol, 1.2 eq) was then added to the solution. The solution was then allowed to stir at 0° for one hour. During this time, a white precipitate formed. 2-amino-4-methyl-6-tert-butylphenol (1.863 g, 10.4 mmol, 1.0 eq), prepared according to the synthesis method described in Example 6, was then added to the suspension. The suspension was then allowed to stir overnight. The next day, the solvent was removed under reduced pressure, and ethyl acetate was added. The resulting suspension was then filtered to remove the solid. The filtrate was washed with 10% citric acid solution (2×50 ml), 5% NaHCO$_3$ (2×50 ml) and brine (50 ml). It was dried over MgSO$_4$, and the solvent was removed under reduced pressure, leaving a solid which was recrystallized from hexane to give the product as a white solid (2.92 g, 7.9 mmol, 76% yield). $^1$H NMR (300 MHz, CDCl$_3$) δ 9.55 (s, 1H), 8.77 (s, 1H), 7.84 (s, 1H), 7.05 (d, J=1.8 Hz, 1H), 6.92 (m, 3H), 2.30 (s, 3H), 2.28 (s, 3H), 2.22 (s, 6H), 1.45 (s, 9H); $^{13}$C NMR (75 MHz, CDCl$_3$) δ 158.5, 157.4, 146.2, 140.6, 138.1, 134.9, 129.9, 129.6, 129.4, 126.9, 124.9, 121.4, 35.3, 30.0, 21.2, 21.0, 18.5. Anal. Calcd for C$_{22}$H$_{28}$N$_2$O$_3$: C, 71.71; H, 7.66; N, 7.60. Found: C, 72.01; H, 8.03; N, 7.36.

EXAMPLE 8

Synthesis of N-(2,6-diisopropylphenyl)-N'-(2-hydroxy-5-methylphenyl)-oxalamide N-(2,6-Diisopropylphenyl)-oxanilic acid ethyl ester (5.14 g, 18.5 mmol, 1.0 eq) and 2-amino-5-methylphenol (2.28 g, 18.5 mmol, 1 eq) were dissolved in toluene (50 ml), forming a suspension. To this suspension was then added triethylamine (2.6 ml, 18.5 mmol, 1 eq). The suspension was then heated to reflux, causing the solids to dissolve. After heating at reflux overnight, the product precipitated. At this point, ethyl acetate was added until the precipitate redissolved. The solution was then washed with 2 M HCl solution (2×100 ml). The aqueous layer was then washed with ethyl acetate, and the combined organic layers were washed with brine (100 ml), and dried over MgSO$_4$. The solvent was then removed under reduced pressure, leaving a yellowish solid. The yellowish solid was then recrystallized from toluene, producing a product, white crystalline solid (5.90 g, 16.6 mmol, 90% yield). $^1$H NMR (300 MHz, CDCl$_3$) δ 9.58 (s, 1H), 8.81 (s, 1H), 7.92 (s, 1H), 7.37 (t, J=7.8 Hz 1H), 7.27 (d, J=0.9 Hz, 1H), 7.23 (d, J=7.8 Hz, 2H), 6.97 (dd, J=8.1, 2.1 Hz, 1H), 6.90 (d, J=8.1 Hz, 1H), 3.02 (septet, J=6.6, 2H), 2.29 (s, 3H), 1.22 (d, J=7.2, 12H); $^{13}$C NMR (75 MHz, CDCl$_3$) δ 158.8, 158.2, 146.0, 130.7, 129.4, 128.7, 124.0, 123.8, 122.6, 119.1, 29.2, 23.9, 20.7. Anal. Calcd for C$_{21}$H$_{26}$N$_2$O$_3$: C, 71.16; H, 7.39; N, 7.90. Found: C, 70.85; H, 7.68; N, 7.73.

EXAMPLE 9

Synthesis of N-(2,6-diisopropylphenyl)-N'-(2-hydroxy-3-(adamant-1-yl)-5-methylphenyl)-oxalamide N-(2,6-Diisopropylphenyl)-N'-(2-hydroxy-5-methylphenyl)-oxalamide (5.59 g, 15.5 mmol, 1.0 eq), prepared according to the synthesis method described in Example 8, and 1-adamantol (2.83 g, 18.6 mmol, 1.2 eq) were dissolved in CH$_2$Cl$_2$ (150 ml), forming a suspension. To this suspension was then added concentrated H$_2$SO$_4$ (1 ml). After addition of the acid, the solids eventually went into solution. After stirring at room temperature for 24 hours, the TLC (9:1 hexanes:ethyl acetate, visualized by UV) showed that most of the starting material had gone to product. At this point, the solvent was removed under reduced pressure, and the resulting solids were redissolved in ethyl acetate (100 ml). The resulting solution was then washed with saturated NaHCO$_3$ (3×50 ml, gas is evolved), and brine, then dried over MgSO$_4$. The solvent was removed under reduced pressure, and the resulting solid was purified via column chromatography to give a product, light yellow solid (3.68 g, 7.5 mmol, 48%). $^1$H NMR (300 MHz, CDCl$_3$) δ 9.51 (s, 1H), 8.77 (s, 1H), 7.84 (s, 1H), 7.37 (t, J=7.2 Hz 1H), 7.23 (d, J=7.5 Hz, 2H), 7.00 (d, J=2.1 Hz, 1H), 6.94 (d, J=1.8 Hz, 1H), 3.01 (septet, J=6.9, 2H), 2.29 (s, 3H), 2.18 (bs, 6H), 2.10 (bs, 3H), 1.80 (bs, 6H), 1.22 (d, J=6.9, 12H); $^{13}$C NMR (75 MHz, CDCl$_3$) δ 158.3, 158.2, 146.2, 145.8, 140.6, 129.9, 129.2, 129.2, 126.8, 124.7, 123.8, 120.9, 40.7, 37.3, 37.1, 29.1, 29.0, 23.6, 20.8. Anal. Calcd for C$_{31}$H$_{40}$N$_2$O$_3$: C, 76.19; H, 8.25; N, 5.73. Found: C, 75.89; H, 8.42; N, 5.37.

EXAMPLE 10

Synthesis of N-(mesityl)-3-(2-hydroxyphenyl)-4,5-dihydro-imidazolium chloride

N-(Mesityl)-N'-(2-hydroxyphenyl)-oxalamide (1.47 g, 4.9 mmol, 1 eq), prepared according to the synthesis method described in Example 3, was weighed into an oven-dried round-bottom flask. To this was added BH$_3$-THF (1M in THF) (39 ml, 39.2 mmol, 8 eq). A great deal of bubbling resulted, as the solution turned bright orange. The solution was allowed to reflux overnight. The next day, the solution was observed to have turned clear. The solution was then allowed to cool to room temperature. Methanol was then very slowly added to the solution until all bubbling ceased. Concentrated HCl solution (1.5 ml) was then added, and the solvent was removed under reduced pressure. The resulting solid was dissolved in methanol, and then the solvent was again removed under reduced pressure. This process was repeated twice more. In this way, the remaining boron was removed as B(OMe)$_3$. Triethylorthoformate (15 ml) was then added to the resulting solid, forming a suspension. The suspension was then heated to 100° C. As the suspension was heated, the solid was observed to slowly go into solution. After aproximately one minute at high temperature, a white solid precipitated. It was allowed to stir for five more minutes, and was then filtered. The resulting solid was washed with ether, to provide the desired product as a white powder (0.854 g, 2.7 mmol, 55% yield). $^1$H NMR (300 MHz, CDCl$_3$) δ 11.43 (s, 1H), 8.84 (s, 1H), 7.54 (dd, J=8.25, 1.2 Hz, 1H), 7.05 (dd, J=8.0, 1.2 Hz, 1H), 6.92 (m, 2H), 6.73 (dt, J=7.7, 0.9 Hz 1H), 4.80 (t, J=11.4 Hz, 2H), 4.37 (t, J=11.7 Hz, 2H), 2.33 (s, 3H), 2.29 (s, 6H); $^{13}$C NMR (75 MHz, CDCl$_3$) δ 157.4, 150.0, 141.0, 135.3, 130.7, 130.3, 128.8, 122.8, 120.4, 119.9, 118.8, 51.0, 50.4, 21.3, 18.2. Anal. Calcd for C$_{18}$H$_{21}$ClN$_2$O: C, 68.24; H, 6.68; N, 8.84. Found: C, 67.86; H, 6.92; N, 8.52.

EXAMPLE 11

Synthesis of 1-(2,6-diisopropylphenyl)-3-(2-hydroxyphenyl)-4,5-dihydro-imidazolium chloride N-(2,6-Diisopropylphenyl)-N'-(2-hydroxyphenyl)-oxalamide (0.7356 g, 2.2 mmol, 1 eq), prepared according to the synthesis method described in Example 4, was treated in a fashion similar to that described in Example 10 for N-(mesityl)-N'-(2-hydroxyphenyl)-oxalamide). The resulting solid was washed with ether, to provide the desired product as a white powder (0.657 g, 1.83 mmol, 85% yield). $^1$H NMR (300 MHz, CDCl$_3$) δ 9.04 (s, 1H), 7.57 (dd, J=8.9, 1.2 Hz, 1H), 7.44 (t, J=7.8 Hz, 1H), 7.22 (d, J=7.8 Hz, 2H), 7.15 (d, J=6.6 Hz, 1H), 6.97 (dt, J=7.8, 1.8 Hz, 1H), 6.78 (dt, J=8.3, 0.9 Hz, 1H), 4.88 (t, J=11.4 Hz, 2H), 4.44 (t, J=11.1, 2H), 2.95 (septet, J=6.6 Hz, 2H), 1.25 (d, J=7.2 Hz, 6H), 1.16 (d, J=6.6 Hz, 6H); $^{13}$C NMR (75 MHz, CDCl$_3$) δ 157.0, 149.8, 146.6, 131.6, 130.0, 128.7, 125.1, 122.6, 120.3, 120.0, 118.6, 52.7, 51.1, 28.9, 25.0, 24.3. Anal. Calcd for C$_{21}$H$_{27}$ClN$_2$O: C, 70.28; H, 7.58; N, 7.81. Found: C, 70.32; H, 7.76; N, 7.63.

EXAMPLE 12

Synthesis of 1-(mesityl)-3-(2-hydroxy-3-tert-butyl-5-methylphenyl)-4,5-dihydro-imidazolium chloride N-(Mesityl)-N'-(2-hydroxy-3-tert-butyl-5-methylphenyl)-oxalamide (2.385 g, 6.5 mmol, 1 eq), prepared according to the synthesis method described in Example 7, was treated in a fashion similar to that described in Example 10 for N-(mesityl)-N'-(2-hydroxyphenyl)-oxalamide). The resulting solid was washed with ether, to provide the desired product as a white powder (0.884 g, 2.28 mmol, 35% yield). $^1$H NMR (300 MHz, CDCl$_3$) δ 8.42 (s, 1H), 7.10 (d, J=1.5 Hz, 1H), 6.96 (s, 2H), 6.80 (s, 1H), 4.79 (t, J=11.1 Hz, 2H), 4.43 (t, J=9.6 Hz, 2H), 2.47 (s, 6H), 2.30 (s, 3H), 2.27 (s, 3H), 1.41 (s, 9H); $^{13}$C NMR (75 MHz, CDCl$_3$) δ 158.7, 148.1, 144.2, 140.7, 135.8, 130.8, 130.6, 130.3, 128.9, 127.5, 121.6, 52.3, 51.6, 35.6, 30.1, 21.2, 21.1, 18.6. Anal. Calcd for C$_{23}$H$_{31}$ClN$_2$O: C, 71.39; H, 8.07; N, 7.24. Found: C, 72.01; H, 8.03; N, 7.36.

EXAMPLE 13

Synthesis of 1-(2,6-diisopropylphenyl)-3-(2-hydroxy-3-(adamant-1-yl)-5-methylphenyl)-4,5-dihydro-imidazolium chloride N-(2,6-Diisopropylphenyl)-N'-(2-hydroxy-3-(adamant-1-yl)-5-methylphenyl)-oxalamide (1.83 g, 3.7 mmol, 1 eq), prepared according to the synthesis method described in Example 9, was treated in a fashion similar to that described in Example 10 for N-(mesityl)-N'-(2-hydroxyphenyl)-oxalamide). The resulting solid was washed with ether, to provide the desired product as a white powder (1.19 g, 2.3 mmol, 63% yield). $^1$H NMR (300 MHz, CDCl$_3$) δ 8.23 (s, 1H), 7.45 (t, J=8.1 Hz, 1H), 7.27 (d, J=8.1 2H), 7.04 (s, 1H), 6.80 (s, 1H), 4.88 (t, J=10.8 Hz, 2H), 4.45 (t, J=11.7 Hz, 2H), 3.41 (septet, J=6.6 Hz 2H), 2.28 (s, 3H), 2.13 (bs, 6H), 2.04 (bs, 3H), 1.74 (m, 6H), 1.34 (d, J=6.9 Hz, 6H), 1.29 (d, J=6.6 Hz, 6H); $^{13}$C NMR (75 MHz, CDCl$_3$) δ 158.4, 148.3, 147.3, 144.4, 131.4, 130.8, 130.2, 128.8, 127.8, 125.2, 121.1, 54.0, 52.4, 40.8, 37.8, 37.2, 29.2, 28.8, 25.5, 24.4, 21.1. Anal. Calcd for C$_{32}$H$_{43}$ClN$_2$O: C, 75.78; H, 8.55; N, 5.52. Found: C, 74.78; H, 8.64; N, 5.44.

EXAMPLE 14

1-(mesityl)-3-(2-hydroxyphenyl)-4,5-dihydro-imidazolium chloride and potassium hexamethyl disilazane (2.1 equiv.) were dissolved in THF (20 ml) at room temperature, giving a cloudy, light yellow solution. This solution was then stirred for minutes. A solution of (PdClMePEt$_3$)$_2$ (0.5 equiv.) in THF was then added, producing a light yellow solution with a precipitate. The solution was then stirred for one hour. The solution was then filtered through celite, and the THF was removed under reduced pressure until roughly 2 ml remained. Pentane (10 mL) was then added to the solution which was then allowed to sit overnight at −40° C. The next day, a white precipitate was observed to have developed. The product was then recovered via filtration.

EXAMPLE 15

1-(2,6-diisopropylphenyl)-3-(2-hydroxyphenyl)-4,5-dihydro-imidazolium chloride and potassium hexamethyl disilazane (2.1 equiv.) were dissolved in THF (20 ml) at room temperature, giving a cloudy, light yellow solution. This solution was then stirred for 5 minutes. A solution of (PdClMePPh$_3$)$_2$ (0.5 equiv.) in THF was then added, producing a light yellow solution with a precipitate. The solution was then stirred for one hour. The solution was then filtered through celite, and the THF was removed under reduced pressure until roughly 2 ml remained. Pentane (10 mL) was then added to the solution which was then allowed to sit overnight at −40° C. The next day, a white precipitate was observed to have developed. The product was then recovered via filtration.

EXAMPLE 16

1-(mesityl)-3-(2-hydroxy-3-tert-butyl-5-methylphenyl)-4,5-dihydro-imidazolium chloride and potassium hexamethyl disilazane (2.1 equiv.) were dissolved in THF (20 ml) at room temperature, giving a cloudy, light yellow solution. This solution was then stirred for 5 minutes. A solution of (PdClMePPh$_3$)$_2$ (0.5 equiv.) in THF was then added, producing a light yellow solution with a precipitate. The solution was then stirred for one hour. The solution was then filtered through celite, and the THF was removed under reduced pressure until roughly 2 ml remained. Pentane (10 mL) was then added to the solution which was then allowed to sit overnight at −40° C. The next day, a white precipitate was observed to have developed. The product was then recovered via filtration.

EXAMPLE 17

1-(2,6-diisopropylphenyl)-3-(2-hydroxy-3-adamantyl-5-methylphenyl)-4,5-dihydro-imidazolium chloride and potassium hexamethyl disilazane (2.1 equiv.) were dissolved in THF (20 ml) at room temperature, giving a cloudy, light yellow solution. This solution was then stirred for 5 minutes. A solution of (PdClMePPh$_3$)$_2$ (0.5 equiv.) in THF was then added, producing a light yellow solution with a precipitate. The solution was then stirred for one hour. The solution was then filtered through celite, and the THF was removed under reduced pressure until roughly 2 ml remained. Pentane (10 mL) was then added to the solution which was then allowed to sit overnight at −40° C. The next day, a white precipitate was observed to have developed. The product was then recovered via filtration.

EXAMPLE 18

1-(2,6-diisopropylphenyl)-3-(2-hydroxy-3-adamantyl-5-methylphenyl)-4,5-dihydro-imidazolium chloride and potassium hexamethyl disilazane (2.1 equiv.) were dissolved in THF (20 ml) at room temperature, giving a cloudy, light yellow solution. This solution was then stirred for 5 minutes. A solution of NiMesBr(PPh$_3$)$_2$ (1 equiv.) in THF was then added, producing a light yellow solution with a precipitate. This solution was then stirred for 1 hour. The solution was then filtered through celite, and the THF was removed under reduced pressure until roughly 2 ml remained. Pentane (10 mL) was then added to the solution, which was then allowed to sit overnight at −40° C. The next day, a yellow precipitate had developed. The product was then recovered via filtration.

EXAMPLE 19

1-(2,6-diisopropylphenyl)-3-(2-hydroxyphenyl)-4,5-dihydro-imidazolium chloride and potassium hexamethyl disilazane (2.1 equiv.) were dissolved in THF (20 ml) at room temperature, giving a cloudy, light yellow solution. This solution was then stirred for 5 minutes. A solution of NiMesBr(PPh$_3$)$_2$ (1 equiv.) in THF was then added, producing a light yellow solution with a precipitate. This solution was then stirred for 1 hour. The solution was then filtered through celite, and the THF was removed under reduced pressure until roughly 2 ml remained. Pentane (10 mL) was then added to the solution, which was then allowed to sit overnight at −40° C. The next day, a yellow precipitate had developed. The product was then recovered via filtration.

EXAMPLE 20

1-(2,6-diisopropylphenyl)-3-(2-hydroxy-3-adamantyl-5-methylphenyl)-4,5-dihydro-imidazolium chloride and potassium hexamethyl disilazane (2.1 equiv.) were dissolved in THF (20 ml) at room temperature, giving a cloudy, light yellow solution. This solution was then stirred for 5 minutes. A solution of TiCl$_4$(thf)$_2$ (0.5 equiv.) in THF was then added, producing a dark red solution with precipitate. This solution was then stirred for 1 hour. The solution was then filtered through celite, and the THF was removed under reduced pressure. The resulting solid was then taken up in diethyl ether and allowed to sit overnight at −40° C. The next day dark red crystals were observed to have developed. The product was then recovered via filtration.

EXAMPLE 21

1-(2,6-diisopropylphenyl)-3-(2-hydroxy-3-adamantyl-5-methylphenyl)-4,5-dihydro-imidazolium chloride and potassium hexamethyl disilazane (2.1 equiv.) were dissolved in tetrahydrofuran (20 ml) at room temperature, giving a cloudy, light yellow solution. This solution was then stirred for 5 minutes. A solution of ZrCl$_4$ (0.5 equiv.) in THF was then added, producing a light yellow solution with precipitate. This solution was then stirred for 1 hour. The solution was then filtered through celite, and the THF was removed under reduced pressure. The resulting solid was then taken up in diethyl ether and was allowed to sit overnight at −40° C. The next day a light yellow precicpitate has developed. The product was then recovered via filtration.

EXAMPLE 22

In a dry box, to a clean, dry reactor cell of an Argonaut Endeavor® containing a disposable glass reaction insert was added 0.438 g (7.50 mmol) solid MAO. The reactor cell was sealed and pressure tested to 400 psig. To the reactor cell was then added 5.0 mL of toluene. Stirring was commenced and the reactor was heated to 65° C. and pressurized with ethylene gas to 400 psig. Upon equilibration of the reactor temperature and pressure, 5.1 mg (5 μmol) bis(1-2,6-diisopropylphenyl)-3-(2-hydroxy-3-adamantyl-5-methylphenyl)-4,5-dihydro-imidazolyl) titanium dichloride dissolved in 0.5 mL toluene was then added to the reactor cell via an addition port. The addition port was then immediately rinsed with an additional 0.5 mL of toluene and the reaction timer was engaged. The reaction was then allowed to proceed for 90 minutes with a continuous ethylene feed. After 90 minutes, the reaction was terminated by venting the excess ethylene gas. The reactor cell was then opened and the glass cell liner and its contents were removed. The glass cell liner and contents were then removed from the dry box and 2–3 mL of acidified MeOH (10 wt % HCl) was slowly and carefully added to the contents of the glass cell liner. After standing for several minutes, the contents of the glass cell liner were dumped into 200 mL rapidly stirred MeOH, where they were kept for one to two hours. The resulting mixture was then washed with excess MeOH and filtered to dryness. Residual solvents were removed by heating the resultant white powder at 60° C. under vacuum for 18 hours to yield 1.84 g of polymer product.

EXAMPLE 23

In a dry box, to a clean, dry reactor cell of an Argonaut Endeavors® containing a disposable glass reaction insert was added 0.292 g (5.00 mmol) solid MAO. The reactor cell was then sealed and pressure tested to 400 psig. To the reactor cell was then added 5.0 mL of toluene. Stirring was commenced and the reactor cell was heated to 65° C. and pressurized with ethylene gas to 400 psig. Upon equilibration of the reactor temperature and pressure, 5.4 mg (5 μmol) bis(1-(2,6-diisopropylphenyl)-3-(2-hydroxy-3-adamantyl-5-methylphenyl)-4,5-dihydro-imidazolyl) zirconium dichloride dissolved in 0.5 mL toluene was added to the reactor cell via an addition port. The addition port was then immediately rinsed with an additional 0.5 mL of toluene and the reaction timer was engaged. The reaction was then allowed to proceed for 90 minutes with continuous ethylene feed. After 90 minutes, the reaction was terminated by venting the excess ethylene gas. The reactor cell was then opened and the glass cell liner and its contents were removed. The glass cell liner and contents were then removed from the dry box and 2–3 mL of acidified MeOH (10 wt % HCl) was slowly and carefully added to the contents of the glass cell liner. After standing for several minutes, the contents of the glass cell liner were dumped into 200 mL of rapidly stirred MeOH, where they were kept for one to two hours. The resulting mixture was then washed with excess MeOH and filtered to dryness. Residual solvents were removed by heating the resultant white powder at 60° C. under vacuum for 18 hours to yield 1.35 g of polymer product.

EXAMPLE 24

In a dry box, to a clean, dry reactor cell of an Argonaut Endeavor® containing a disposable glass reaction insert was added 0.438 g (7.50 mmol) solid MAO. The reactor cell was then sealed and pressure tested to 400 psig. To the reactor cell was then added 5.0 mL of toluene. Stirring was then commenced and the reactor cell was heated to 65° C. and pressurized with ethylene gas to 400 psig. Upon equilibration of the reactor temperature and pressure, 4.6 mg (5 μmol) 1-(2,6-diisopropylphenyl)-3-(2-hydroxy-3-adamantyl-5-methylphenyl)-4,5-dihydroimidazolyl methyl triphenylphosphine nickel dissolved in 0.5 mL of toluene was added to the reactor cell via an addition port. The addition port was then immediately rinsed with an additional 0.5 mL toluene and the reaction timer was engaged. The reaction was then allowed to proceed for 90 minutes with continuous ethylene feed. After 90 minutes, the reaction was terminated by venting the excess ethylene gas. The reactor cell was then opened and the glass cell liner and its contents were removed. The glass cell liner and contents were then removed from the dry box and 2–3 mL of acidified MeOH (10 wt % HCl) was slowly and carefully added to the contents of the glass cell liner. After standing for several minutes, the contents of the glass cell liner were dumped into 200 mL rapidly stirred MeOH, where they were kept for one to two hours. The resulting mixture was then washed with excess MeOH and filtered to dryness. Residual solvents were removed by heating the resultant white powder at 60° C. under vacuum for 18 hours to yield 0.35 g of polymer product.

EXAMPLE 25

In a dry box, to a clean, dry reactor cell of an Argonaut Endeavor® containing a disposable glass reaction insert was added 0.292 g (5.00 mmol) solid MAO. The reactor cell was then sealed and pressure tested to 400 psig. To the reactor cell was then added 1.0 mL of a norbornene/toluene solution (79 wt % norbornene in toluene) followed by 4.0 mL of toluene. Stirring was then commenced and the reactor cell was heated to 65° C. and pressurized with ethylene gas to 400 psig. Upon equilibration of the reactor temperature and pressure, 5.1 mg (5 μmol) bis(1-(2,6-diisopropylphenyl)-3-(2-hydroxy-3-adamantyl-5-methylphenyl)-4,5-dihydro-imidazolyl) titanium dichloride dissolved in 0.5 mL of toluene was added to the reactor cell via an addition port. The addition port was then immediately rinsed with an additional 0.5 mL of toluene and the reaction timer was engaged. The reaction was then allowed to proceed for 120 minutes with continuous ethylene feed. After 90 minutes, the reaction was terminated by venting the excess ethylene gas. The reactor cell was opened and the glass cell liner and its contents were removed. The glass cell liner and contents were then removed from the dry box and 2–3 mL of acidified MeOH (10 wt % HCl) was slowly and carefully added to the contents of the glass cell liner. After standing for several minutes, the contents of the glass cell liner were dumped into 200 mL rapidly stirred MeOH, where they were kept for one to two hours. The resulting mixture was then washed with excess MeOH and filtered to dryness. Residual solvents were removed by heating the resultant white powder at 60° C. under vacuum for 18 hours to yield 2.69 g of polymer product.

EXAMPLE 26

In a dry box, to a clean, dry reactor cell of an Argonaut Endeavor® containing a disposable glass reaction insert was added 0.292 g (5.00 mmol) solid MAO. The reactor cell was then sealed and pressure tested to 400 psig. To the reactor cell was then added 1.0 mL of a norbornene/toluene solution (79 wt % norbornene in toluene) followed by 4.0 mL of toluene. Stirring was then commenced and the reactor was heated to 65° C. and pressurized with ethylene gas to 400 psig. Upon equilibration of the reactor temperature and pressure, 5.4 mg (5 mmol) bis(1-(2,6-diisopropylphenyl)-3-(2-hydroxy-3-adamantyl-5-methylphenyl)-4,5-dihydro-imidazolyl) zirconium dichloride dissolved in 0.5 mL toluene was added to the reactor cell via an addition port. The addition port was then immediately rinsed with an additional 0.5 mL of toluene and the reaction timer was engaged. The reaction was then allowed to proceed for 120 minutes with continuous ethylene feed. After 90 minutes, the reaction was terminated by venting the excess ethylene gas. The reactor cell was then opened and the glass cell liner and its contents were removed. The glass cell liner and contents were then removed from the dry box and 2–3 mL of acidified MeOH (10 wt % HCl) was slowly and carefully added to the contents of the glass cell liner. After standing for several minutes, the contents of the glass cell liner were dumped into 200 mL rapidly stirred MeOH, where they were kept for one to two hours. The resulting mixture was then washed with excess MeOH and filtered to dryness. Residual solvents were then removed by heating the resultant white powder at 60° C. under vacuum for 18 hours to yield 1.30 g of polymer product.

EXAMPLE 27

In a dry box, to a clean, dry reactor cell of an Argonaut Endeavor® containing a disposable glass reaction insert was added 0.292 g (5.00 mmol) solid MAO. The reactor cell was sealed and pressure tested to 400 psig. To the reactor cell was then added 1.0 mL of a norbornene/toluene solution (79 wt % norbornene in toluene) followed by 4.0 mL of toluene. Stirring was then commenced and the reactor was heated to 65° C. and pressurized with ethylene gas to 400 psig. Upon equilibration of the reactor temperature and pressure, 6.8 mg (7.5 µmol) 1-(2,6-diisopropylphenyl)-3-(2-hydroxy-3-adamantyl-5-methylphenyl)-4,5-dihydroimidazolyl methyl triphenylphosphine nickel dissolved in 0.5 mL toluene was then added to the reactor cell via an addition port. The addition port was then immediately rinsed with an additional 0.5 mL of toluene and the reaction timer was engaged. The reaction was then allowed to proceed for 120 minutes with continuous ethylene feed. After 90 minutes, the reaction was terminated by venting the excess ethylene gas. The reactor was then opened and the glass cell liner and its contents were removed. The glass cell liner and contents were then removed from the dry box and 2–3 mL of acidified MeOH (10 wt % HCl) was slowly and carefully added to the contents of the glass cell liner. After standing for several minutes, the contents of the glass cell liner were dumped into 200 mL rapidly stirred MeOH, where they were kept for one to two hours. The resulting mixture was then washed with excess MeOH and filtered to dryness. Residual solvents were then removed by heating the resultant white powder at 60° C. under vacuum for 18 hours to yield 0.15 g of polymer product.

What is claimed is:

1. A polymerization catalyst comprising:
a metal center selected from Ti Zr and Hf with at least one chelating ligand comprising a carbene with an anionic moiety, wherein the at least one chelating ligand has a structure selected from

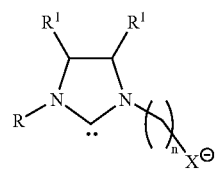
(I)

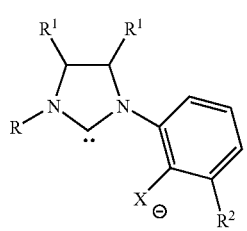
(II)

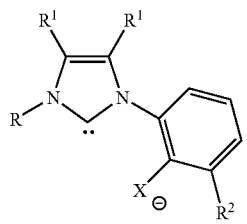
(IV)

wherein R is any hydrocarbyl group; each $R_1$ is independently any hydrocarbyl group; $R^2$ is any hydrocarbyl group; n is selected from 1 and 2; and X is selected from O, N and S; and wherein both the carbene and the anionic moiety are coordinated to the metal center.

2. The polymerization catalyst of claim 1, wherein the polymerization catalyst comprises two chelating ligands.

3. The polymerization catalyst of claim 2, further comprising two halide ligands, wherein the halide ligands are each independently selected from Cl, Br and I.

4. A process for preparing a homopolymer or copolymer comprising contacting at least one α-olefin monomer with the polymerization catalyst of claim 2 in the presence of an aluminum activator.

5. A process for preparing a copolymer comprising contacting the polymerization catalyst of claim 2 with at least two different monomers selected from α-olefins, norbornene, norbornene containing a pendent hydrocarbyl substituent and styrene in the presence of an aluminum activator.

6. A process for preparing a homopolymer or copolymer comprising:
providing a polymerization catalyst comprising a metal center selected from Ti, Zr, Hf, Ni and Pd with at least one chelating ligand comprising a carbene with an anionic moiety, wherein the at least one chelating ligand has a structure selected from

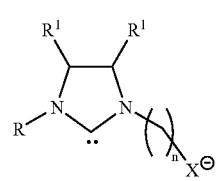
(I)

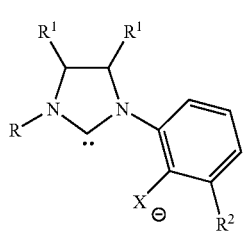
(II)

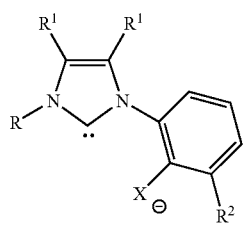
(IV)

wherein R is any hydrocarbyl group; each $R^1$ is independently any hydrocarbyl group; $R^2$ is any hydrocarbyl group; n is selected from 1 and 2; and X is selected from O, N and S; wherein both the carbene and the anionic moiety are coordinated to the metal center; and with the proviso that when the metal center is Ni or Pd the polymerization catalyst comprises one of the at least one chelating ligand;

providing ethylene; and, contacting the ethylene with the polymerization catalyst.

7. The process of claim 6, further comprising:

providing at least one monomer selected from α-olefins, norbornenes and styrene;

providing an aluminum activator; and, contacting the ethylene and the polymerization catalyst with the at least one monomer selected from α-olefins, norbornenes and styrene in the presence of the aluminum activator.

8. The process of claim 6, wherein the polymerization catalyst further comprises a hydrocarbyl ligand and a neutral ligand coordinated with the metal center; wherein the hydrocarbyl ligand is selected from Me, Ph and Mesityl and the neutral ligand is selected from phosphine, amine and pyridine.

9. The process of claim 6, wherein the polymerization catalyst further comprises a chelating hydrocarbyl ligand coordinated with the metal center.

* * * * *